United States Patent [19]

Hedges et al.

[11] 4,163,116
[45] Jul. 31, 1979

[54] PROCESS FOR PRODUCING BISPHENOLS

[75] Inventors: Charles V. Hedges, Mt. Vernon; Victor Mark, Evansville, both of Ind.

[73] Assignee: General Electric Company, Pittsfield, Mass.

[21] Appl. No.: 876,706

[22] Filed: Feb. 10, 1978

[51] Int. Cl.$^2$ .................... C07C 37/00; C07C 37/12
[52] U.S. Cl. .................................................. 568/723
[58] Field of Search ........................................ 568/723

[56] References Cited

U.S. PATENT DOCUMENTS

| | | | |
|---|---|---|---|
| 1,977,627 | 10/1934 | Greenhalgh | 568/728 |
| 2,060,716 | 11/1936 | Arvin | 568/723 |
| 2,602,822 | 7/1952 | Schwartzer et al. | 568/723 |
| 2,623,908 | 12/1952 | Stoesser et al. | 568/728 |
| 2,653,979 | 9/1953 | Kropa et al. | 568/723 |
| 2,858,343 | 10/1958 | Hoaglin et al. | 568/723 |
| 3,057,928 | 10/1962 | Koblitz et al. | 568/723 |
| 3,242,219 | 5/1966 | Farnhan et al. | 568/728 |
| 3,382,283 | 5/1968 | Zundel et al. | 568/723 |

*Primary Examiner*—Norman Morgenstern
*Attorney, Agent, or Firm*—Morgan, Finnegan, Pine, Foley & Lee

[57] ABSTRACT

Bisphenols, substantially free of by-products, are produced rapidly by reacting a phenol and a compound of the formula

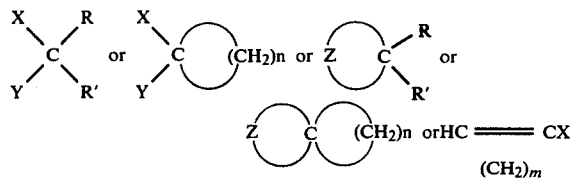

wherein R and R' are independently selected from the group consisting of hydrogen, lower alkyl or aryl; X is lower acyloxy; Y is lower alkoxy, aryloxy or the same as X; Z is the divalent radical

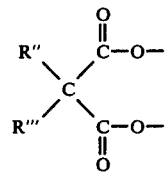

wherein R" and R'" are selected from the same category as R and R', and n is an integer from 3 to 9; $m=(n-1)$.

11 Claims, No Drawings

PROCESS FOR PRODUCING BISPHENOLS

The present invention relates to the preparation of highly pure bisphenols.

BACKGROUND OF THE INVENTION

It is well known that bisphenols, such as bisphenol-A, can be obtained by the interaction of phenol with acetone or other ketones in the presence of acidic condensing agents. These processes, however, have yielded products contaminated with a large number of by-products, such as chromans, spiro compounds, linear or cyclic dimers of isopropenylphenols and compounds of more complex structures which are generally unsuitable for technical operations without extensive and difficult time—and energy—consuming purification steps.

It has now been discovered that excellent yields of highly pure bisphenols can be obtained by substituting for the acetone or other ketone reactant a compound containing as an essential structural feature, an arrangement of carbon and oxygen atoms of any of the following structural formulae

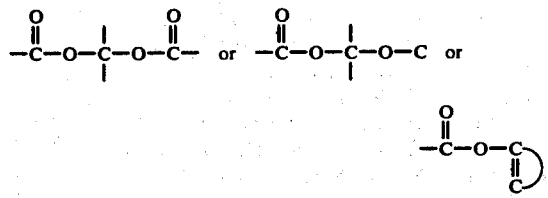

It has been discovered that the reaction is very fast near room temperature ($\sim 30°$ C.), and, except for the o,p' isomer (with phenol as the reactant) only very small amounts of contaminants are formed when "p,p'-bisphenol-A" is the desired product. In any event, the by-products, including the o,p' isomer, are easily removed by a simple slurrying of the separated solids with methylene chloride.

DESCRIPTION OF THE INVENTION

According to this invention condensation is effected by acid catalysis between at least equivalent quantities of a phenol, preferably having a reactive hydrogen para to the phenolic hydroxyl, and a compound of the formula

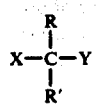    I wherein R and R' are hydrogen, (lower) alkyl or aryl; X is (lower aliphatic or aromatic) acyloxy; Y is (lower) alkoxy, aryloxy or the same as X.

The condensation is effected with facility also with compounds where R and R' are part of a common cycle, such as in

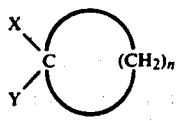    II where n is an integer from 3 to 9, and X and Y are as defined above; or with compounds where X and Y are part of a common cycle, such as in

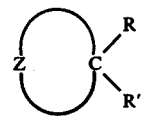    III where Z is the divalet radical

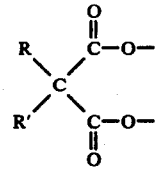

where R and R' are the same as above or with compounds represented by the combination of formulae II and III as in IV

    IV or with compounds of formula II where Y is represented by unsaturation as in V

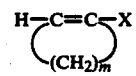    V where m is $(n-1)$.

Compounds represented by general formulae I to V can be considered as masked carbonyls which yield with phenols under acid catalysis the same compounds as the unmasked carbonyl compounds do, without, however, producing the self-condensation products of the latter, which are responsible for the numerous by-products encountered in the reaction of the free carbonyl-bearing reactants. Also, the reactions with phenols of compounds represented by I to V are much faster than those of the conventional carbonyl compounds.

The compounds represented by formulae I to IV can be obtained from carbonyl compounds and organic acids under mineral acid catalysis. Compounds represented by I, Y being alkoxy or aryloxy are obtained on heating the corresponding unsaturated ether with the organic acid at higher temperatures. Compounds represented by formula V are best obtained by the transesterification of the corresponding cyclic ketone with isopropenyl acetate or by the thermolysis of the corresponding precursor with structure II.

It is a preferred feature of the invention to react phenol with 2,2-diacetoxy propane,

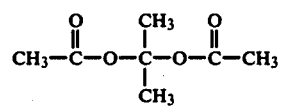

to produce bisphenol-A. It is also a preferred feature to react phenol with 1-acetoxycyclohexene to produce 4,4'-cyclohexylidenediphenol:

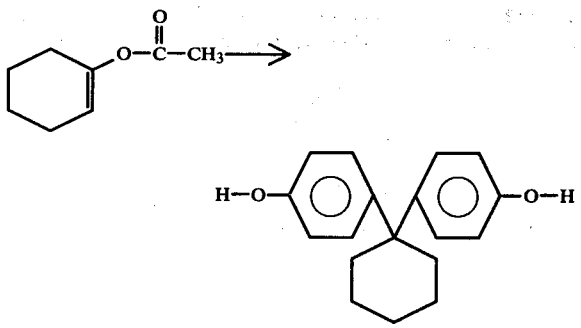

While the reaction in general can be carried out at temperatures between about 0° C. and 100° C., it is usually carried out at temperatures between 15° C. and 80° C., preferably in the range of from about 20° C. to about 65° C., and especially preferably from about 30° C. to about 50° C. at atmospheric or super-atmospheric pressure.

The reaction can be carried out in the absence or in the presence of solvents, such as methylene chloride, 1,2-dichloroethane, benzene, toluene and the like. An especially preferred solvent is the phenol reactant itself, which is thus used in an excess of the stoichiometric proportion. The avoidance of foreign solvents greatly simplifies workup and permits a direct recycling of the phenol.

Any conventional acidic condensing agent can be used, preferably one which is soluble in the phenol employed, e.g., hydrogen chloride, hydrogen bromide, mixtures thereof, sulfuric acid, or phenol-insoluble ones, such as acidic ion exchange resins, and the like. When gaseous hydrogen chloride is used, superatmospheric pressures provide for faster reaction rates.

The condensation reaction can be catalyzed by hydrogen sulfide, mercaptans, thiophenols or compounds with free—SH group. Solid catalysts, such as the acidic ion exchange resins may also be modified by sulfhydryl and groups. The term "(lower) alkanoyl" contemplates alkanoyl groups of from about 2 to about 7 carbon atoms, in which the alkane radicals are straight chain or branched, e.g., acetyl, n-propionyl, i-butyroyl, and the like.

The phenol is employed in from an equivalent amount, e.g., at least 2 moles, and preferably at least 3 moles of phenol per mole of the second reactant. For convenience and economy, the phenol is usually employed in an amount of from 3 to 12 moles per mole of the second reactant.

In practice, with a volatile condensing agent, such as HCl, the phenol is melted and the condensing agent is added thereto, suitably in an amount sufficient to maintain the reaction mixture saturated thereto with respect to the condensing agent at a reaction temperature between 15° and 100° C., superatmospheric pressures are advantageously employed. Either prior to or after adding the acid condensing agent, the second reactant can be mixed in the desired proportions. Condensation is continued preferably until the reaction product typically forms, or consists of, a slurry of crystals comprising the bisphenol in unreacted phenol. The acidic condensation agent can be removed and then the product recovered in a conventional way, e.g., by filtration, centrifugation and the like. Heating the crystalline material which often is a complex of the bisphenol with phenol, in a vacuum will remove unreacted starting materials, and washing with phenol or, preferably, methylene chloride, will remove by-products.

To avoid unnecessary detailed description, conventional techniques for making bisphenols employing phenol and acetone are illustrated in Greenhalgh, U.S. Pat. No. 1,977,627; Stoesser et al, U.S. Pat. No. 2,623,908; and Farnham et al, U.S. Pat. No. 3,242,219, the disclosures of which are incorporated herein by reference.

DESCRIPTION OF THE PREFERRED EMBODIMENTS

The invention is illustrated but not limited by the following examples.

EXAMPLE 1

To a solution of 292 g (3.0 moles) of phenol and 43.6 g (0.3 mole) of 1,1-diacetoxyethane (boiling point 167°-169° C.; which can be prepared by reacting acetaldehyde with acetic anhydride and phosphoric acid), was introduced at 40° a slow stream of anhydrous hydrogen chloride. External cooling was applied to maintain the termperature of the mildly exothermic reaction between 38° and 48° C. Gas chromatographic analysis of a sample, taken one hour after the introduction of hydrogen chloride started, indicated that the reaction was complete. Removal of the catalyst and acetic acid at 14 mm pressure resulted in a liquid that on cooling to ambient temperature deposited the adduct of the diphanel and phenol. Filtration of the solids and decomposition of the phenol-diphanol adduct at 80° to 160° C. and 14 mm pressure by distilling off phenol, resulted in a white residue that had the following composition by gas chromatographic analysis:

| Compound | Retention time (min.) | Composition (mole %) |
|---|---|---|
| 2,4'-Ethylidenediphenol | 16.29 | 1.8 |
| 4,4'-Ethylidenediphenol | 17.30 | 98.2 |
| p-Cumylphenol (reference) | 13.80 | |

One recrystallization from benzene yielded 4,4'-ethylidenediphenol, melting point 123° to 125° C., that was 99.8% pure by gas chromatography.

EXAMPLE 2

The procedure of Example 1 was exactly repeated, accept that 1,1-diacetoxyethane was replaced by the equivalent amount (48.0 g, 0.3 mole) of 1,1-diacetoxypropane. The solid diphenol-phenol adduct, that was filtered off and from which phenol was removed by vacuum distillation, yielded a crude diphenol with the following composition by gas chromatography:

| Compound | Retention time (min.) | Composition (mole %) |
|---|---|---|
| 2,4'-Propylidenediphenol | 16.69 | 1.7 |
| 4,4'-Propylidenediphenol | 17.40 | 98.3 |
| p-Cumylphenol (reference) | 13.95 | |

One recrystallization from benzene yielded 4,4'-propylidenediphenol, melting point 131° to 133° C., that was 99.9% pure by gas chromatography.

EXAMPLE 3

The procedure of Example 1 was repeated, except that 1,1-diacetoxyethane was replaced by the equivalent amount (48.0 g, 0.3 mole) of 2,2-diacetoxypropane, boiling point 62° C. at 25 mm pressure (which can be prepared by reacting isopropenyl orthoformate with acetic acid). After the removal of acetic acid in water aspirator vacuum, the solid adduct that was deposited at ambient temperature, was filtered and decomposed by heating in vacuum to yield phenol and a white residue with the following composition:

| Compound | Retention time (min.) | Composition (mole %) |
| --- | --- | --- |
| 2,4'-Isopropylidenediphenol (o,p'-BPA) | 16.48 | 1.9 |
| 4,4'-Isopropylidenediphenol (p,p'-BPA) | 17.85 | 98.1 |
| p-Cumylphenol (reference) | 13.98 | |

EXAMPLE 4

The procedure of Example 1 was exactly repeated, except that 1,1-diacetoxyethane was replaced with an equivalent amount (43.2 g, 0.3 mole) of 2,2-dimethyl-1,3-dioxan-4,6-dione,

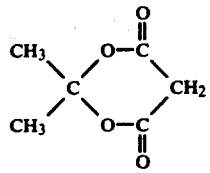

melting point 94° to 95° C. (which is readily available from acetone and malonic acid by acid catalysis, with the removal of water). The mildly exothermic reaction (maximum temperature 51° C.) was over in ½ hour. A sample taken of the warm, liquid reaction mixture, one hour later, contained the following products (analysis by gas chromatography):

| Compound | Retention Time (min.) | Composition (mole %) |
| --- | --- | --- |
| 2,4'-Isopropylidenediphenol (o,p'-BPA) | 16.50 | 2.2 |
| "Chroman-I"[1] | 17.55 | 1.0 |
| 4,4-Isopropylidenediphenol (p,p'-BPA) | 17.90 | 96.8 |
| p-Cumylphenol (reference) | 13.98 | |

[1]"Chroman-I" has the following structure:

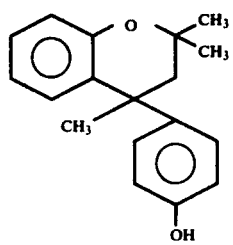

EXAMPLE 5

The procedure of Example 4 was repeated, except that the cyclic acylal was replaced with the equivalent amount (55.3 g 0.3 mole) of 2,2-pentamethylene-1,3-dioxan-4,6-dione, melting point 95°-96°,

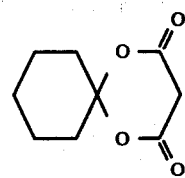

(available from cyclohexanone and malonic acid via acid catalysis and water removal). At the end of the reaction phenol was removed by vacuum distillation and the solid residue analyzed by gas chromatography, which showed the following composition:

| Compound | Retention time (min.) | Composition (mole %) |
| --- | --- | --- |
| 2,4'-Cyclohexylidenediphenol | 21.90 | 8.9 |
| 4,4'-Cyclohexylidenediphenol | 23.42 | 91.1 |
| p-Cumylphenol (reference) | 15.71 | |

Recrystallization from aqueous methanol yielded 4,4'-cyclohexylidenediphenol (Bisphenol-C), mp 188°, in 99.3% purity.

EXAMPLE 6

Repeating the procedure of Example 5, except for replacing the bicyclic acylal with the equivalent amount of 1-acetoxycyclohexene (42.0 g, 0.3 mole), yielded 4,4'-cyclohexylidenediphenol in comparable yield and purity to that shown in the example.

EXAMPLE 7

Repeating the procedure of Example 2, except for replacing phenol with the equivalent amount of o-cresol (324 g, 3.0 moles), yielded, at the end of the reaction, the following composition:

| Compound | Retention time (min.) | Composition (mole %) |
| --- | --- | --- |
| 6,6'-Propylidenedi-o-cresol | 18.20 | 1.4 |
| 4,6'-Propylidenedi-o-cresol | 18.44 | 13.1 |
| 4,4'-Propylidenedi-o-cresol | 19.22 | 83.5 |
| Higher tricresol | 26.52 | 2.0 |
| p-Cumylphenol (reference) | 14.10 | | from which the pure 4,4'-isomer was isolated by recrystallization from benzene, melting point 94°-95° C.

The above description is illustrative only. Any variation therefrom which conforms to the spirit of the invention is intended to be included within the scope of the claims.

We claim:

1. A process for the production of bisphenols which comprises reacting a phenol containing at least one reactive hydrogen and a compound of the formula

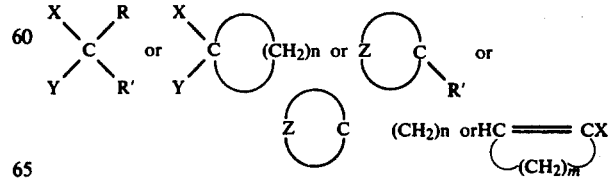

wherein R and R' are independently selected from the group consisting of hydrogen, lower alkyl or aryl; X is lower acyloxy; Y is lower alkoxy, aryloxy or the same as X; Z is the divalent radical

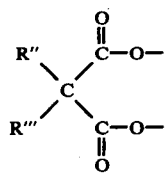

wherein R" and R''' are independently selected from the same group as R and R', and n is an integer from 3 to 9; m=(n−1), or a mixture of such compounds, in the presence of a acidic condensing agent.

2. A process as defined in claim 1 wherein said phenol has a reactive hydrogen para to the phenolic hydroxyl.

3. A process as defined in claim 2 wherein phenol is reacted with 2,2-diacetoxypropane to produce bisphenol-A.

4. A process as defined in claim 2 wherein phenol is reacted with cyclohexenyl acetate to produce bisphenol-C.

5. A process as defined in claim 1 wherein the temperature of reaction is maintained in the range of from about 20° C. to about 65° C.

6. A process as defined in claim 1 wherein the acidic condensing agent is hydrogen chloride.

7. A process as defined in claim 1 which also includes the steps of separating the bisphenol product in solid form and washing the solid produce with methylene chloride until substantially free of by-products.

8. A process for the production of bisphenol-A which comprises reacting phenol and 2,2-diacetoxypropane in the presence of hydrogen chloride at a temperature of from about 20° to about 50° C.

9. A process as defined in claim 8 which further includes separating the bisphenol-A in solid form from the reaction mixture, and washing the solid product with methylene chloride until substantially free of by-products.

10. A process for the production of bisphenol-C which comprises reacting phenol and cyclohexenyl acetate in the presence of hydrogen chloride at a temperature of from about 30° to about 50° C.

11. A process as defined in claim 10 which further includes separating the bisphenol-C in solid form from the reaction mixture and washing the solid product with methylene chloride until substantially free of by-products.

* * * * *

UNITED STATES PATENT AND TRADEMARK OFFICE
CERTIFICATE OF CORRECTION

PATENT NO. : 4,163,116
DATED : July 31, 1979
INVENTOR(S) : Charles V. Hedges and Victor Mark It is certified that error appears in the above-identified patent and that said Letters Patent are hereby corrected as shown below:

In the Abstract, latter part of first formula, connecting parenthesis were omitted -- formula should read

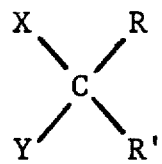 or 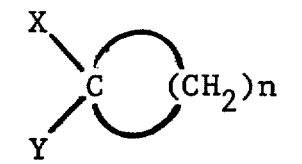 or 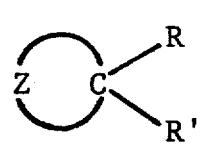 or

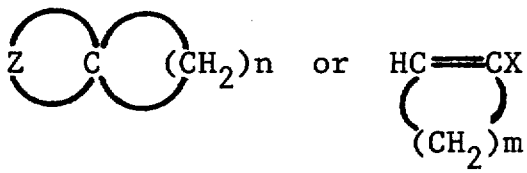 or HC≡≡CX 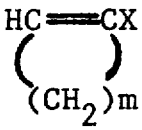

UNITED STATES PATENT AND TRADEMARK OFFICE
CERTIFICATE OF CORRECTION

PATENT NO. : 4,163,116
DATED : July 31, 1979
INVENTOR(S) : Charles V. Hedges and Victor Mark It is certified that error appears in the above-identified patent and that said Letters Patent are hereby corrected as shown below:

Column 4, line 16, "292 g" should read -- 282 g --.

Signed and Sealed this

Twenty-fifth Day of December 1979

[SEAL]

Attest:

Attesting Officer

SIDNEY A. DIAMOND

Commissioner of Patents and Trademarks